(12) United States Patent
Eberlein et al.

(10) Patent No.: US 6,626,943 B2
(45) Date of Patent: Sep. 30, 2003

(54) ARTIFICIAL INTERVERTEBRAL DISC

(75) Inventors: Robert Eberlein, Volken (CH); Simon Casutt, Gossau (CH); Markus Fröhlich, Balterswil (CH)

(73) Assignee: Sulzer Orthopedics Ltd., Baar (CH)

( * ) Notice: Subject to any disclaimer, the term of this patent is extended or adjusted under 35 U.S.C. 154(b) by 21 days.

(21) Appl. No.: 10/226,517

(22) Filed: Aug. 23, 2002

(65) Prior Publication Data

US 2003/0045940 A1 Mar. 6, 2003

(30) Foreign Application Priority Data

Aug. 24, 2001 (EP) .............................. 01810827

(51) Int. Cl.[7] .................................................. A61F 2/44
(52) U.S. Cl. .................................................... 623/17.15
(58) Field of Search .......................... 623/17.11, 17.12, 623/17.13, 17.14, 17.15; 606/61

(56) References Cited

U.S. PATENT DOCUMENTS

| | | | | |
|---|---|---|---|---|
| 3,867,728 A | * | 2/1975 | Stubstad et al. ................. 3/1 |
| 4,911,718 A | * | 3/1990 | Lee et al. ....................... 623/17 |
| 4,932,969 A | * | 6/1990 | Frey et al. ..................... 623/17 |
| 5,002,576 A | * | 3/1991 | Fuhrmann et al. ............. 623/17 |
| 5,458,642 A | * | 10/1995 | Beer et al. ..................... 623/17 |
| 5,674,294 A | * | 10/1997 | Bainville et al. .............. 623/17 |
| 5,674,296 A | * | 10/1997 | Bryan et al. ................... 623/17 |
| 5,683,465 A | | 11/1997 | Shinn et al. |
| 5,989,291 A | * | 11/1999 | Ralph et al. ................... 623/17 |
| 6,063,121 A | * | 5/2000 | Xavier et al. .................. 623/17 |
| 6,402,785 B1 | * | 6/2002 | Zdeblick et al. .......... 623/17.16 |

FOREIGN PATENT DOCUMENTS

| | | |
|---|---|---|
| DE | 200 19 520 U1 | 3/2001 |
| EP | 0 346 269 A2 | 12/1989 |
| FR | 2 787 015 | 6/2000 |
| FR | 2 787 018 | 6/2000 |
| WO | 00/35385 | * 6/2000 |

* cited by examiner

Primary Examiner—Bruce Snow
(74) Attorney, Agent, or Firm—Christie, Parker & Hale, LLP

(57) ABSTRACT

The invention relates to an artificial intervertebral disc for implantation between two vertebral bodies (W) comprising two end plates (1, 2) and an elastically deformable disc (3) pre-stressed between the end plates (1, 2) in the axial direction, with the disc (3) lying within a tubular, elastically deformable, fibre ring (4) and the end plates (1, 2) being in tensile communication with the fibre ring (4). The disc (3) has a contact surface (5, 6) which enlarges with a compression of the artificial intervertebral disc and which adjoins one of the end plates (1, 2) so that the elastic properties of the artificial intervertebral disc show a non-linear behaviour with increasing deformation at least with respect to a compression force (F).

19 Claims, 5 Drawing Sheets

ARTIFICIAL INTERVERTEBRAL DISC

CROSS-REFERENCE TO RELATED APPLICATION

Figure 1:
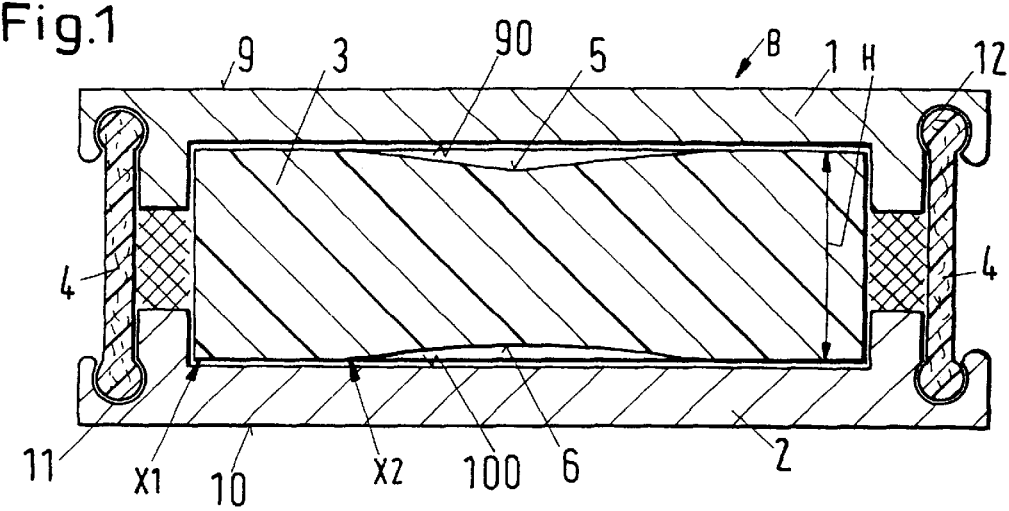

This application claims priority of European Patent Application No. 01 810 827.4, filed on Aug. 24, 2001.

The invention relates to an artificial intervertebral disc for implantation between two vertebral bodies comprising two end plates and an elastically deformable disc pre-stressed between the end plates in the axial direction with the disc lying within a tubular, elastically deformable, fibre ring and the end plates being in tensile connection with the fibre ring.

The intervertebral disc takes on a plurality of central functions simultaneously in the vertebral column. It functions as a damper, a spacer body and also as a joint between the vertebral bodies. The demands to be made on an implant which is intended to serve as a replacement for a natural intervertebral disc in its function as an artificial intervertebral disc are correspondingly complex. For instance, the artificial intervertebral disc must naturally be made up of biocompatible materials and, as a permanent implant, must fulfil its function for the patient for life where possible. In addition to the simple function as a spacer body, the artificial intervertebral disc must in particular be able to effectively cushion the impact forces occurring in the vertebral column so that the vertebrae are not subject to excess stress—however, without noticeably hindering the movability of the vertebrae. A fixed connection must be ensured between the artificial intervertebral disc and the adjoining vertebra in order to suitably lead off the natural stresses of turning, tilting and shearing such as typically occur in the vertebral column.

The highest demands are thus to be made, in particular on the elastic properties of the artificial intervertebral disc, both as regards its behaviour with respect to torsional and shear stresses and with respect to pressure stresses. Overall, this means that the mechanical properties of the artificial intervertebral disc have to be reproduced as identically as possible to those of the natural intervertebral disc.

Numerous approaches are known for the replication of the natural properties of an intervertebral disc. For instance, artificial intervertebral discs are known which consist of two end plates, which are oppositely arranged, which are connected via an elastic support element, which takes over the function of an artificial nucleus and is adhesively bonded to the end plates. The artificial nucleus can, in this respect, consist of a combination of different elastic plastics which can also have a jacket. The hitherto unsolved problem of such arrangements, however, also lies in reproducing the suitable, that is the natural, very non-linear, characteristics of an intervertebral disc in the usual stress range for pressure stresses, tension stresses, shear stresses and torsional stresses in an artificial intervertebral disc.

It is therefore the object of the invention to propose an artificial intervertebral disc which reproduces the complex, elastic properties of a natural intervertebral disc as exactly as possible.

The artificial intervertebral disc which satisfies this object is characterised by the features of independent claim 1. The dependent claims relate to particularly advantageous embodiments of the invention.

The artificial intervertebral disc of the invention for implantation between two adjacent vertebral bodies comprises two end plates and an elastically deformable disc pre-stressed between the end plates in the axial direction, with the disc lying within a tubular, elastically deformable, fibre ring. The end plates are in this respect in tensile connection with the fibre ring. The disc forms a contact surface with one of the adjacent end plates which becomes larger with a compression of the artificial intervertebral disc and the elastic properties of the artificial intervertebral disc show a non-linear behaviour with increasing deformation at least with respect to a compression force.

In the artificial intervertebral disc of the invention, two opposite end plates are connected at their peripheries by means of an elastically deformable fibre ring which exerts a constant tensile force on the end plates in the unstressed state such that the disc, which is located between the two end plates within the fibre ring, is under pressure pre-stress. A substantial disadvantage of known artificial intervertebral discs lies in the fact that under the effect of an elastic deformation too long a path is stressed until the actual stress region is reached. A decisive advantage of the artificial intervertebral disc of the invention can therefore be seen in the fact that its elastic behaviour shows a non-linear behaviour at even small deformations at least with respect to compression.

The elastic behaviour of the artificial intervertebral disc of the invention is in this respect determined by the special design features of the fibre ring and the disc and in particular by the design-determined mechanical coupling of the fibre ring and the disc. For instance, the mechanical behaviour of the fibre ring with respect to elongation under tensile stress and elongation, for example, as a result of torsional stresses can already be different due to the type of fabric structure, depending on whether the fibre ring was woven, knitted, braided or manufactured in another manner. In this respect, among other things, the orientation of the fibres, of which the fibre ring is made up, in their slanting position with respect to the direction of the longitudinal axis of the artificial intervertebral disc play a roll for the forces to be transferred between the end plates. Whereas the disc alone, that is not in combination with the fibre ring, forms only a sliding friction resistance, for example with respect to pure torsional movements, a conversion of, for example, torsional movements into a compression of the disc can be achieved by the combination of both elements and an opposed slanting position of the fibres relative to the direction of the longitudinal axis of the artificial intervertebral disc. In this way, the non-linear elastic properties which the disc has with respect to a compression are transformed into the elastic torsional behaviour of the artificial intervertebral disc. The disc is under a certain pressure pre-stress via the fibre ring in the unstressed state. The possibility thus exists to adapt the elastic properties to the individual needs of a patient while observing a pre-determined geometry for the artificial intervertebral disc and without changing or replacing the materials which make up the artificial intervertebral disc. In this manner, the non-linear stress characteristics can be matched, for example, to the body weight of the patient and/or the coupling of torsional strains or other kinds of strain to a compression of the disc.

The type of construction with a fibre ring stressed by tension and a disc stressed by pressure allows the pres-stress between these two elements in the unstressed state to be selected to be so high that at extreme pressure strain, for example 4000 N, there is still a residual stress present in the tension direction which has a co-effect on a limitation of additional shear and torsional strains. Furthermore, it can be achieved (for example by the geometry of the disc in combination with a suitable choice of the pre-stress of the fibre ring) that the artificial intervertebral disc has a certain elastic neutral zone for small strains with respect to tilting and bending movements.

The materials which make up the fibre ring include biocompatible plastics to the extent that they come into contact with body tissue. The fibre ring itself can be permeable for the body's own liquids. The end plates can be made of a metal, for example of robust titanium, or of a robust titanium alloy, which is plastically deformable for the anchoring of the fibre tube. The outer surfaces of the end plates can have zones with a metal web which facilitate the ingrowth of bone material and thus the growing together of the adjoining vertebrae with the outer surfaces of the end plates. An improvement of the anchoring between the end plate and the vertebra with respect to lateral forces is achieved by one or more projecting ribs which extend, for example, from ventral to dorsal. An additional toothed arrangement at the outer edge of the end plate, which—like the projecting rib—does not have to be present mandatorily, can likewise substantially improve the connection between the end plate and the vertebra with respect to shear stresses. In this respect, the end plate does not necessarily have to be made up of metal, but suitable biocompatible plastics can, for example, also be considered as materials for the composition of the end plate.

Figure 2:
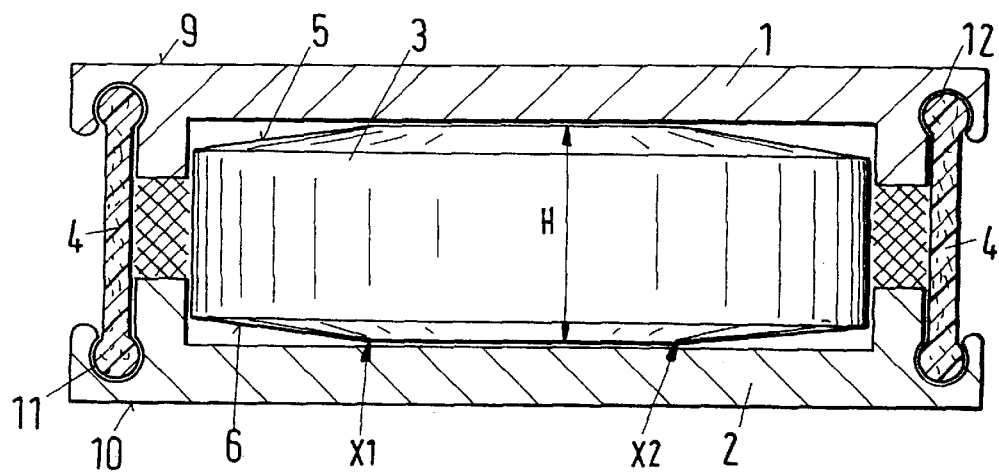
Figure 3:
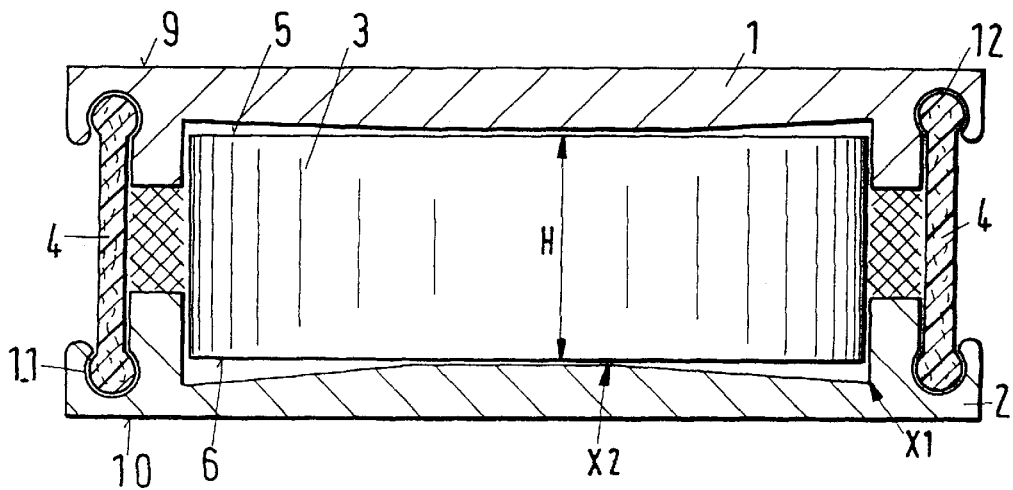
Figure 4:
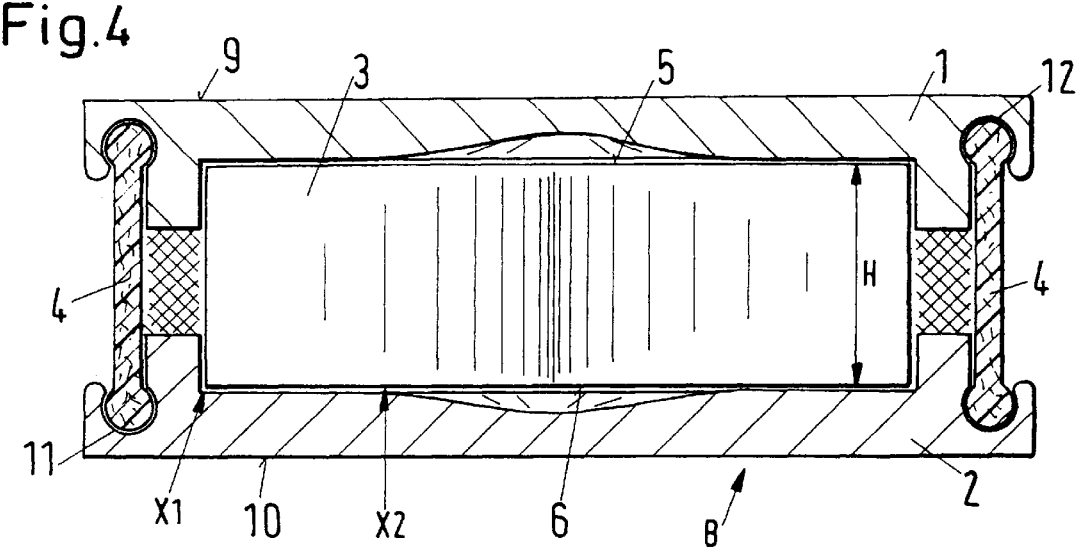
Figure 5:
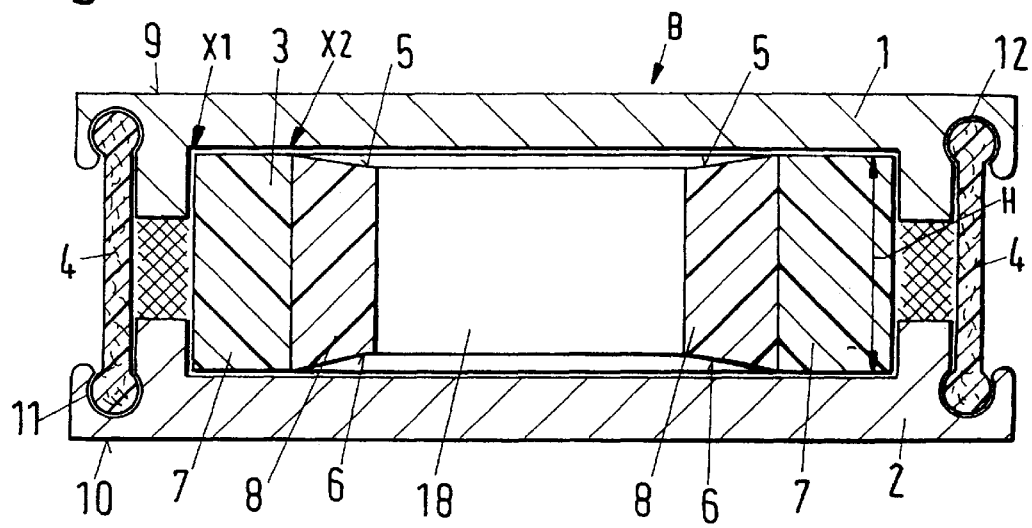
Figure 6:
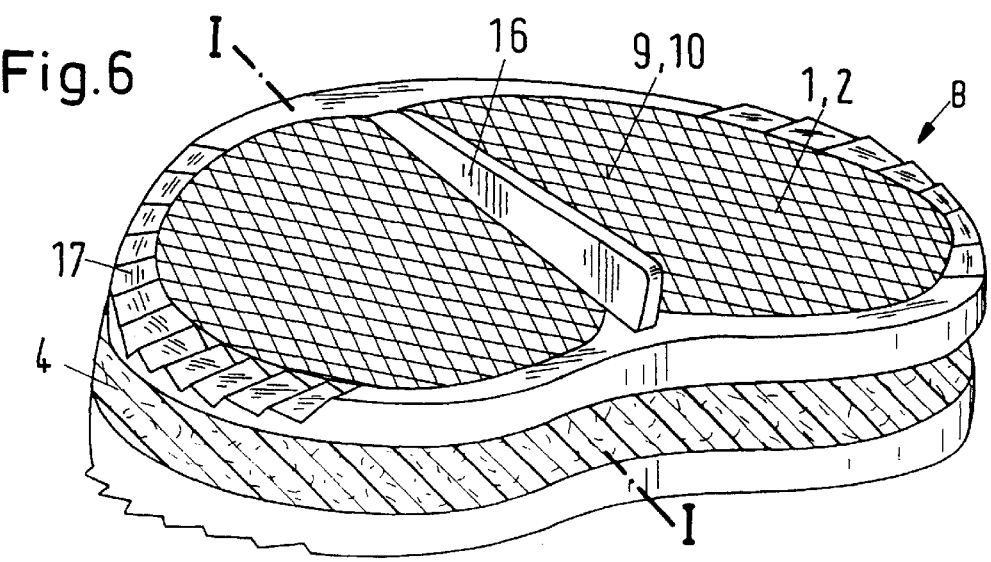
Figure 7:
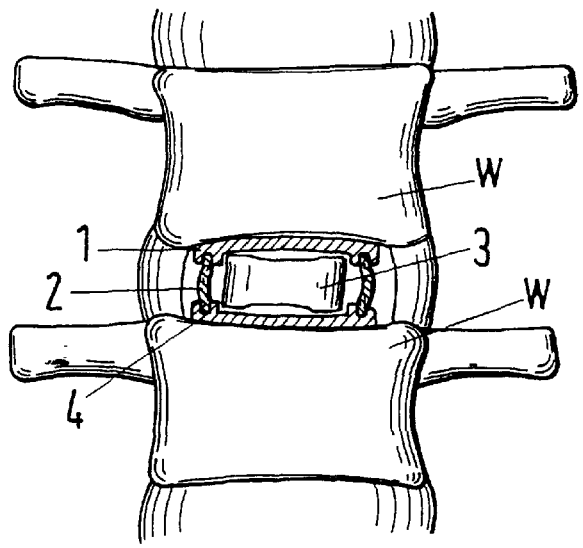
Figure 8:
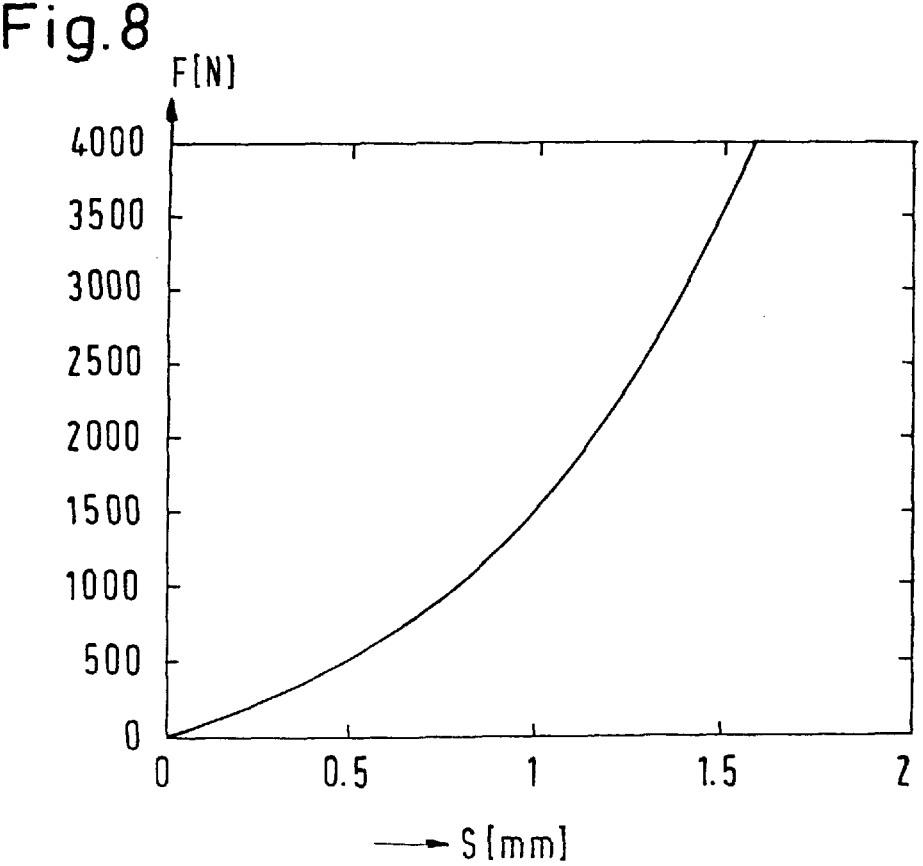
Figure 9:
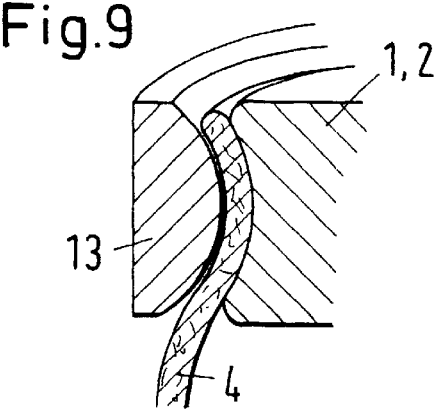
Figure 11:
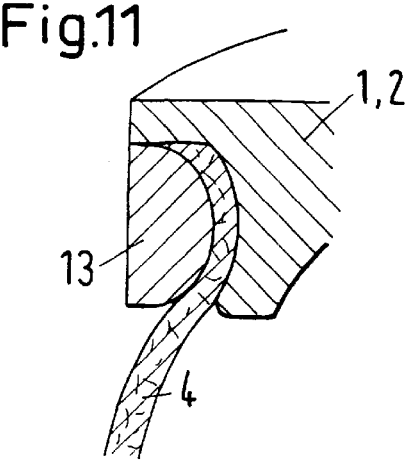
Figure 10:
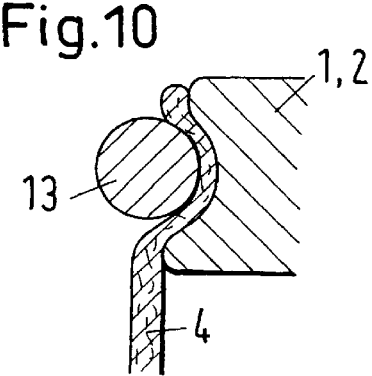
Figure 12:
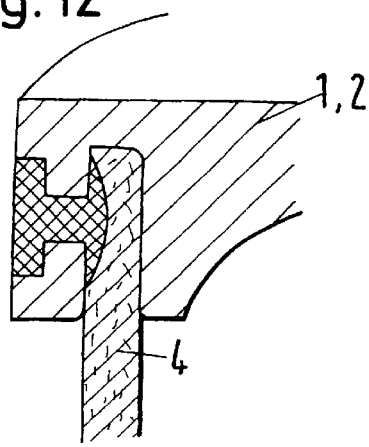
Figure 13:
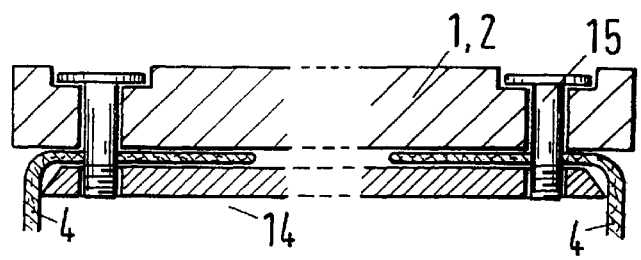
Figure 14:
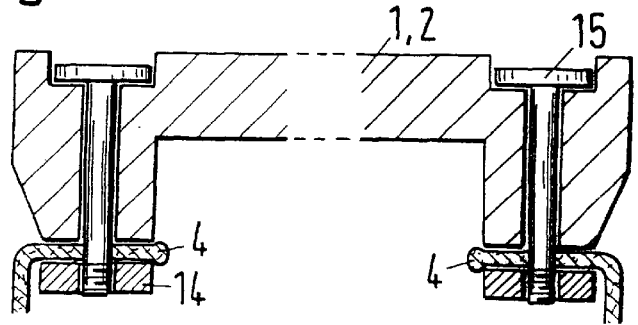
Figure 15:
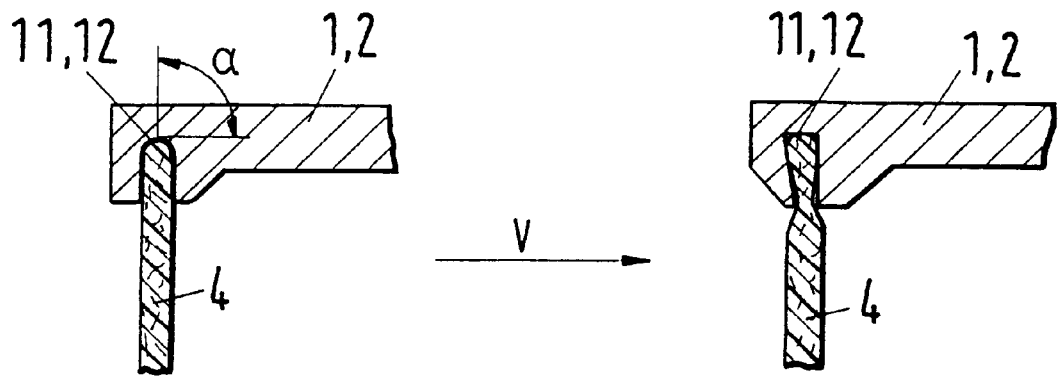
Figure 16:
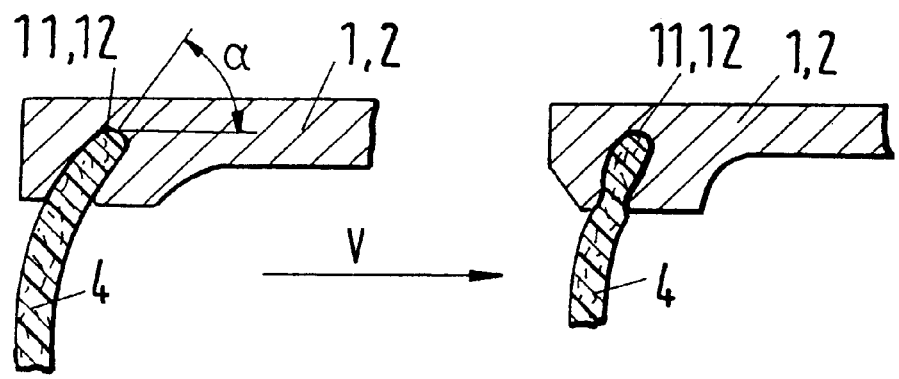
Figure 17:
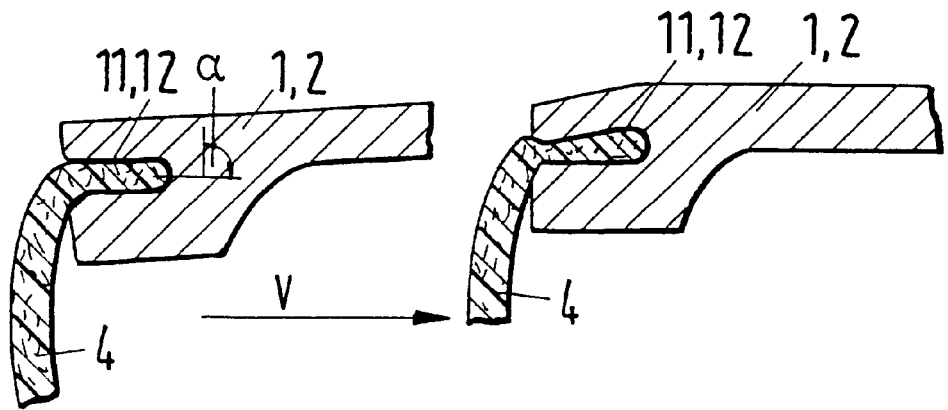

The invention is explained in more detail in the following with reference to preferred embodiments and to the drawing. There are shown:

FIG. 1 schematically, a longitudinal section through a first variant of an artificial intervertebral disc of the invention;

FIG. 2 a second variant of the embodiment in accordance with FIG. 1;

FIG. 3 a third variant of the embodiment in accordance with FIG. 1;

FIG. 4 a fourth variant of the embodiment in accordance with FIG. 1;

FIG. 5 another variant of the embodiment in accordance with FIG. 1;

FIG. 6 schematically, a view in accordance with FIGS. 1 to 5;

FIG. 7 an artificial intervertebral disc of the invention in accordance with FIGS. 1 to 6 inserted between two vertebral bodies;

FIG. 8 force-path diagram of the elastic behaviour of an artificial intervertebral disc of the invention;

FIG. 9 an embodiment to connect the fibre ring to an end place by means of an annular clamping element;

FIG. 10 a second variant of an embodiment in accordance with FIG. 9;

FIG. 11 a third variant of an embodiment in accordance with FIG. 9, with the fibre ring being additionally adhesively bonded or welded;

FIG. 12 an embodiment to connect the fibre ring to an end plate, with the fibre ring being adhesively bonded, welded or injection moulded;

FIG. 13 an embodiment to connect the fibre ring to an end plate, with the fibre ring being fixed by a holding element;

FIG. 14 a further embodiment in accordance with FIG. 13;

FIG. 15 an embodiment to connect the fibre ring to an end plate, with the fibre ring being cold pressed in a groove;

FIG. 16 a second embodiment in accordance with FIG. 15;

FIG. 17 a third embodiment in accordance with FIG. 15.

The invention is explained in the following with reference to preferred embodiments. The artificial intervertebral disc B of the invention comprises two end plates 1, 2 between which a disc 3 is pre-stressed in the axial direction by a fibre ring 4, whereby the end plates 1, 2 are in tensile connection, with the disc 3 having a contact surface 5, 6 with one of the adjoining end plates 1, 2 which increases under pressure strain. The elastic properties of the artificial intervertebral disc B show a non-linear behaviour with increasing deformation S at least with respect to a compression force F.

FIG. 1 shows a preferred embodiment of an artificial intervertebral disc B of the invention in a schematic illustration. A disc 3 is pre-stressed in the radial direction between the end plates 1, 2 whose inner sides 90, 100 are formed as planar surfaces. The height H of the disc 3 of the preferred embodiment from FIG. 1 reduces from the outside to the inside in the radial direction, with, however, the height H also initially remaining constant at the edge between X1, X2 in the unstressed condition. The distance from X1 to X2 depends on the size of the shear modulus of the disc in the vicinity of X1, with the shear modulus of the disc 3 reducing from the outside to the inside in the radial direction. The elastic disc 3 is compressed under a compression force F under a compression force F which acts on the artificial intervertebral disc B perpendicular to the surfaces 1, 2, with the contact surface 5, 6 enlarging between the disc 3 and the inner surface 90, 100 of the cover plate 1, 2. Since the shear modulus of the disc 3 increases from the outside to the inside in the radial direction, the stiffness of the artificial intervertebral disc B increases overall as the compression increases. This behaviour is shown in FIG. 8 in which the deformation S of an artificial intervertebral disc B of the invention under a compression force F is entered by way of example in the form of a force-path diagram, with a greater stiffness meaning that a larger force F is needed for a defined fixedly pre-set deformation S of the artificial intervertebral disc B than for the same deformation S with a lower stiffness. This means that the stiffness corresponds to the increase in the curve of FIG. 8. A higher stiffness corresponds to a higher increase of the curve. For instance, the stiffness of the artificial intervertebral disc B of the invention lies, for example, in a range between 1,700 N/mm and 4,500 N/mm under a compression force of approximately 2,500 N. It is a particular characteristic of the force-path diagram in FIG. 8 that, analogously to the behaviour of a natural intervertebral disc, the start increase of the curve has a positive value different to zero. That is, the artificial intervertebral disc B of the invention shows a value different to zero already with a compression force F which can be as small as desired and thus with stresses which can be as small as desired, with the build height of the artificial intervertebral disc B of the invention either being constant or, for example, reducing from anterior to posterior. This can be realised, for example, by the height H of the disc 3 reducing, for example, from anterior to posterior or by the thickness of the end plates 1, 2 varying accordingly. It can be achieved in this way, among other things, that the elastic behaviour of the artificial intervertebral disc B is not symmetrical with respect to flexion and extension movements.

Since the non-linear properties of the disc B, which shows these with respect to a compression force F, are also transformed by the fibre ring 4 into the torsional and bending behaviour, the artificial intervertebral disc B shows a certain starting stiffness with respect to torsional and bending movements even with corresponding deflections from the unloaded state which can be small as desired. Since the said starting stiffness is achieved in that the disc 3 is under a certain pressure pre-stress via the fibre ring 4 in the unloaded state, the possibility arises of matching the elastic properties to the individual needs of a patient while maintaining a pre-determined geometry for the artificial intervertebral disc B and without changing or replacing the materials making up the artificial intervertebral disc B. In this way, the non-linear strain characteristic and thus the stiffness and its change as the compression force F increases can be matched, for example to the body weight of the patient simply by a suitable selection of the pressure pre-stress in accordance with the demands which are individually defined by the build of the patient.

The non-linear properties of the disc 3 with respect to a compression force F are essentially achieved by the combination of two features. First, the contact surface 90, 100 between the disc 3 and the end plate 1, 2 increases as the compression path S increases. Second, the shear modulus of the disc 3 increases in the radial direction such that the stiffness of the artificial intervertebral disc becomes larger as the compression increases. The characteristics of the elastic behaviour can thus also be fixed, as is shown by way of example in FIG. 8, via the geometry of the disc 3, for example by variation of the width of the region between X1 and X2. The non-linear properties of the disc 3 can also be set by a suitable selection of the materials from which the disc is built up. Furthermore, the amount of the increase of the shear modulus of the disc 3 in the radial direction can be fixed or varied in different ways. The disc 3 can, for example, be built up of silicon elastomers or rubber materials such as polycarbo-urethane (PCU). Such materials can be injection moulded on for the manufacture of the disc 3 and post-pressed with different force in the different regions of the disc 3, whereby regions of different stiffness can be produced in the disc 3. Another possibility of modelling the non-linear behaviour of the disc 3 consists of building up the disc 3 concentrically from rings of different materials, which have different stiffness, the rings being mutually effectively fixedly connected. In this respect, the disc 3 can, as shown in FIG. 5, be built up of ring parts 7, 8 mutually effectively fixedly connected such that the ring parts 7, 8 surround a hollow space 18. The formation of the hollow space 18 is, however, in no way absolutely necessary, that is the hollow space 18 can also be omitted.

Various variants are feasible for the formation of the surface 5, 6 which increases under a compression force F. For instance, the surface 90, 100 of the end plate 1, 2 facing inwards can, as shown in FIGS. 1, 2, 5, display an essentially planar surface. The height H of the surface 3 then reduces in the radial direction either from the outside to the inside (see FIG. 1 and FIG. 5) or from the inside to the outside (see FIG. 2), with the height H also remaining constant in the unstressed state over the region between X1 and X2. Further variants are shown in FIGS. 3 and 4. In these variants of the preferred embodiment, the height H of the disc 3 is constant. Instead, the spacing of the cover plate 1, 2 to the disc 3 varies in the radial direction either from the inside to the outside or vice versa. The variants shown in FIGS. 1, 4, 5 show a particularly high stability with respect to tilt strains while the variants shown in FIGS. 2 and 3 can have a larger flexural elasticity. Suitable combinations of the embodiments described above are naturally also possible.

The requirement for a good functioning of the artificial intervertebral disc B of the invention is a perfect anchoring of the fibre ring 4 in the end plate 1, 2. A groove 11, 12 in the end plate 1, 2 is shown schematically in FIGS. 9 to 12 and in FIGS. 15 to 17, in which the fibre ring 4 is secured. The kind of securing depends, among other things, on the material of the end plate 1, 2. For instance, the fibre ring 4 can, as shown in FIGS. 9, 10, be fixed to the end plate 1, 2, which is made of metal or of plastic, in the groove 11, 12, for example by an annular clamping element 13, and/or be additionally (see FIGS. 11, 12) adhesively bonded in the groove 11, 12. With the end plate 1, 2 of plastic, thermal welding in the groove 11, 12 or at a surface of the end plate 1, 2 is also possible as an alternative to adhesive bonding. With a metallic end plate 1, 2, the fibre ring 4 can be pressed in the groove 11, 12 by cold forming V. In this respect, the groove 11, 12 can, as shown in FIGS. 15 to 17, be inclined at a defined angle α against the surface of the end plate 1, 2, with an angle α being selected which lies between 0 degrees (FIG. 17) and 90 degrees (FIG. 15), preferably however in the vicinity of 30 degrees. As a further variant for the securing of the fibre ring 4 to the end plate 1, 2, a fixing by means of an additional holding element 14 is also feasible, that can be made, for example, as a plate (FIG. 13) or as a ring (FIG. 14) and that is preferably secured to the end plate 1, 2 by means of a screw connection 15.

A further important point is the anchoring of the artificial intervertebral disc B in the human spinal column at an adjacent vertebra W (see FIG. 7). For instance, an improvement in the anchoring between the end plate 1, 2 and the adjoining vertebra W can be substantially improved with respect to lateral forces by one or more projecting ribs 16 which extend, for example, from ventral to dorsal. An additional toothed arrangement 17 at the outer rim of the cover plate 1, 2 likewise improves the connection between the cover and the vertebra, in particular with respect to shear strains. Zones of metal braid, preferably of titanium or titanium alloys, can be applied to the outer sides of the end plates 1, 2 and facilitate or promote the ingrowth of bone material at the vertebrae.

What is claimed is:

1. An artificial intervertebral disc for implantation between two vertebral bodies (W) comprising two end plates (1, 2) and an elastically deformable disc (3) pre-stressed between the end plates (1, 2) in the axial direction, with the disc (3) lying within a tubular, elastically deformable, fibre ring (4) and the end plates (1, 2) being in tensile connection with the fibre ring (4), wherein the disc (3) has a contact surface (5, 6) with one of the adjoining end plates (1, 2) which enlarges with a compression of the artificial intervertebral disc, and the elastic properties of the artificial intervertebral disc shown a non-linear behavior with increasing deformation at least with respect to a compression force (F).

2. An artificial intervertebral disc in accordance with claim 1, wherein the value for the stiffness of the artificial intervertebral disc under a compression force (F) of 2,500 N lies in a range between 1,700 N/mm and 4,500 N/mm.

3. An artificial intervertebral disc in accordance with claim 1, wherein the shear modulus of the disc (3) increases in the radial direction such that the stiffness of the artificial intervertebral disc likewise increases with an increasing compression force (F).

4. An artificial intervertebral disc in accordance with claim 1, wherein the fibre ring (4) consists of a fabric, a knitted fabric or a braid and comprises one or more layers.

5. An artificial intervertebral disc in accordance with claim 1, wherein the materials building up the fibre ring (4) comprise one or more plastics such as polyamide, polyimide, carbon fibres or polyether etherketone (PEEK), preferably polyethylene terephthalate (PET).

6. An artificial intervertebral disc in accordance with claim 1, wherein the disc (3) comprises two concentrically arranged ring parts (7, 8) mutually effectively fixedly connected.

7. An artificial intervertebral disc in accordance with claim 1, wherein the materials building up the disc (3) comprise silicon elastomers or rubber materials.

8. An artificial intervertebral disc in accordance with claim 1, wherein the end plates (1, 2) consist of a metal, preferably of titanium, of a titanium alloy or of plastic.

9. An artificial intervertebral disc in accordance with claim 1, wherein the end plates (1, 2) are formed as anchoring platforms in order to achieve a growing together of the adjoining vertebral bodies (W) with the outwardly directed areas (9, 10) of the end plates (1, 2).

10. An artificial intervertebral disc in accordance with claim 1, at which one of the end plates (1, 2) has a groove (11, 12) extending in the peripheral direction in order to receive the fibre ring (4).

11. An artificial intervertebral disc in accordance with claim 10, at which the fibre ring (4) is pressed in one of the grooves (11, 12) by cold forming (V) for the connection to one of the end plates (1, 2).

12. An artificial intervertebral disc in accordance with claim 10, at which the fibre ring (4) is fixed by an annular clamping element (13) in one of the grooves (11, 12) for the connection to one of the end plates (1, 2).

13. An artificial intervertebral disc in accordance with claim 1, at which the fibre ring (4) is fixed by a holding element (14), preferably by means of a screw connection (15), for the connection to one of the end plates (1, 2).

14. An artificial intervertebral disc in accordance with claim 10, at which the fibre ring (4) is adhesively bonded or welded in one of the grooves (11, 12) for the connection to one of the end plates (1, 2).

15. An artificial intervertebral disc in accordance with claim 10, at which the fibre ring (4) is injection moulded with plastic in an annular manner in one of the grooves (11, 12) of the end plates (1, 2) for the connection to one of the end plates (1, 2).

16. An artificial intervertebral disc in accordance with claim 1, at which the fibre ring (4) is injection moulded with plastic for the connection to one of the end plates (1, 2) at one of the surfaces (9, 10) thereof.

17. An artificial intervertebral disc in accordance with claim 1, wherein the end plates (1, 2) have a projecting central rib (16), which extends.

18. An artificial intervertebral disc in accordance with claim 1, wherein the end plates (1, 2) have a toothed arrangement (17) directed to the vertebra (W) at its outer rim such that a form-locked connection is achieved by the ingrowth of bone material for the transmission of torsional, bending and shear forces.

19. An artificial intervertebral disc in accordance with claim 1, wherein the pre-stress under which the disc (3) is put by the fibre ring (4) in the unloaded state is so high that with a maximum pressure stress, the fibre ring (4) still always has a positive residual stress in the tension direction.

* * * * *